(12) United States Patent
Krause

(10) Patent No.: US 7,927,299 B2
(45) Date of Patent: Apr. 19, 2011

(54) KNEE BRACE

(76) Inventor: David A. Krause, Cicero, NY (US)

( * ) Notice: Subject to any disclaimer, the term of this patent is extended or adjusted under 35 U.S.C. 154(b) by 591 days.

(21) Appl. No.: 12/023,472

(22) Filed: Jan. 31, 2008

(65) Prior Publication Data

US 2009/0198164 A1    Aug. 6, 2009

(51) Int. Cl.
*A61F 13/00* (2006.01)
(52) U.S. Cl. .............. 602/26; 602/16; 602/23
(58) Field of Classification Search .......... 602/5, 16, 602/23, 26, 27; D24/190, 191
See application file for complete search history.

(56) References Cited

U.S. PATENT DOCUMENTS

| 4,262,664 | A | 4/1981 | Wolfer et al. |
| 4,726,362 | A | 2/1988 | Nelson |
| 4,751,920 | A | 6/1988 | Mauldin et al. |
| 4,991,571 | A | 2/1991 | Kausek |
| 5,749,840 | A | 5/1998 | Mitchell et al. |
| 5,792,086 | A | 8/1998 | Bleau et al. |
| 5,857,989 | A | 1/1999 | Smith, III |
| 6,960,177 | B2 | 11/2005 | Turrini et al. |
| 2003/0153853 | A1* | 8/2003 | Houser .................... 602/16 |
| 2003/0204156 | A1 | 10/2003 | Nelson et al. |
| 2004/0054307 | A1* | 3/2004 | Mason et al. ............ 602/16 |
| 2007/0083136 | A1 | 4/2007 | Einarsson |
| 2010/0056967 | A1* | 3/2010 | Nace ........................ 602/16 |

FOREIGN PATENT DOCUMENTS

EP    1829507    9/2007

OTHER PUBLICATIONS http://jointhealing.com/pages/productpages/brace_seelction.html#arthritis.
www.ski-injury.com/brace.htm.
wvvw.kneeshop.com/proddetail.asp?prod=006XX%2F008XX.
wvvw.kneeshop.com/proddetail.asp?prod=11%2D144X%2DX.
wwvv.sunandski.com/Seirus_Hyperflex_Bionic_Knee_p/0093064035350.htm.
www.kneeshop.com/proddetail.asp?prod=11%2D9096%2Dx%2D26000.

* cited by examiner

*Primary Examiner* — Kim M Lewis
(74) *Attorney, Agent, or Firm* — George R. McGuire; Blaine T. Bettinger; Bond Schoeneck & King, PLLC

(57) ABSTRACT

A knee brace having a hinge assembly comprising an upper segment; a lower segment; a middle linking segment coupled to the upper and lower segments to permit pivotal movement of the upper segment relative to the lower segment; and one or more biasing members anchored to the upper and middle linking segments to resiliently bias the upper and middle segments toward a predetermined alignment. A series of straps connected to the hinge assembly allow attachment of the knee brace to the wearer's leg.

24 Claims, 3 Drawing Sheets

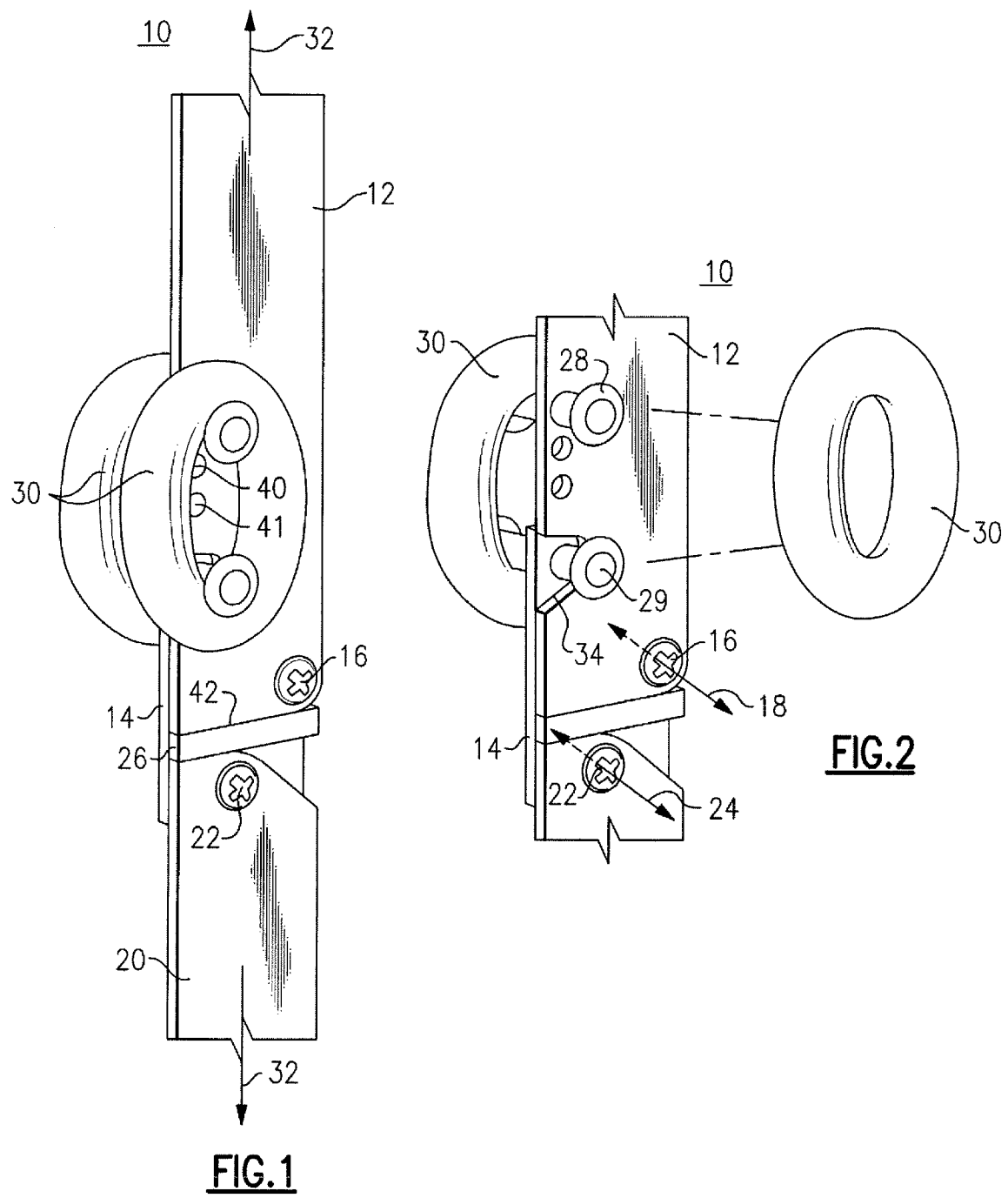

US 7,927,299 B2

KNEE BRACE

BACKGROUND

The present invention relates generally to knee braces, and more particularly to a flexible knee brace to be used during sports or other activity.

Knee braces are typically used by athletes and persons engaged in vigorous physical activity to protect the knee from injury and to avoid exacerbation of existing injury. There are different types of knee braces, depending upon the need and protection required.

Prophylactic braces are used as primary prevention, to stop an injury occurring in the first instance. These braces are usually hinged (either on one side or both sides) and their aim is to prevent excessive movement in the knee joint when an abnormal force is applied to it. These movements may be front to back, side to side or rotational in nature. Rehabilitation braces are used under the supervision of an orthopedic surgeon and/or a physical therapist to control the amount of movement the knee joint is allowed to make, usually after an operation. The idea is that this protects the healing ligament(s) and promotes recovery.

Functional braces are mainly used to protect the anterior cruciate ligament (ACL), either after surgery for those who have had a ligament reconstruction performed, or after injury in those who decide against surgery or who are still waiting for their operation. They aim to reduce rotational and front to back movements, the forces that are associated with injury to the ACL.

Many of the knee braces on the market today include a "hinge and shell" or a "hinge and strap" design. The first kind of brace incorporates molded shells of plastic and foam connected by a hinge system whereas the latter uses leg and thigh straps for attachment. All of the aforementioned braces require protection such as padding along the medial and lateral sides to support and stabilize the knee. Many of the braces prevent and/or restrict certain movement of the knee.

It is a primary object of the invention to provide a knee brace that does not restrict the knee during active movement. It is another object of the invention to provide a knee brace that is lightweight, comfortable and of simple construction. It is a further object of the invention to provide a flexible knee brace that allows repeated flexing and straightening of one's knee during wear. It is yet another object of the invention to provide a knee brace that assists one in straightening one's knees, after flexing one's knees, repeatedly, in activities such as skiing, that require repeated flexing and straightening of one's knees.

SUMMARY OF THE INVENTION

These and other objects and advantages are accomplished by a knee brace that serves to assist the wearer in repositioning his flexed knee to an extended position when engaging in sports or activity.

Specifically, in one embodiment, the knee brace comprises a hinge assembly having an upper segment, a lower segment, a middle linking segment coupled to the upper and lower segments to permit pivotal movement of the upper segment relative to the lower segment, and one or more biasing members anchored to the upper and middle linking segments to resiliently bias the upper and middle segments toward a pre-determined alignment. A series of straps are connected to the hinge assembly to strap the upper, lower and middle segments to a wearer's leg.

In use, the biasing members in the knee brace force the segments in the brace to re-align, which in turn assist the wearer in realigning his legs from a flexed position to an extended position. The knee brace is lightweight, allowing for a full range of motion of the wearer's legs and easy to slip on and take off.

BRIEF DESCRIPTION OF THE DRAWINGS

The present invention will be more fully understood and appreciated by reading the following Detailed Description in conjunction with the accompanying drawings, in which:

FIG. 1 is a perspective view of the knee brace of the present invention;

FIG. 2 is a perspective view of the knee brace showing an exploded view of the hinge section;

DETAILED DESCRIPTION

Figure 3:
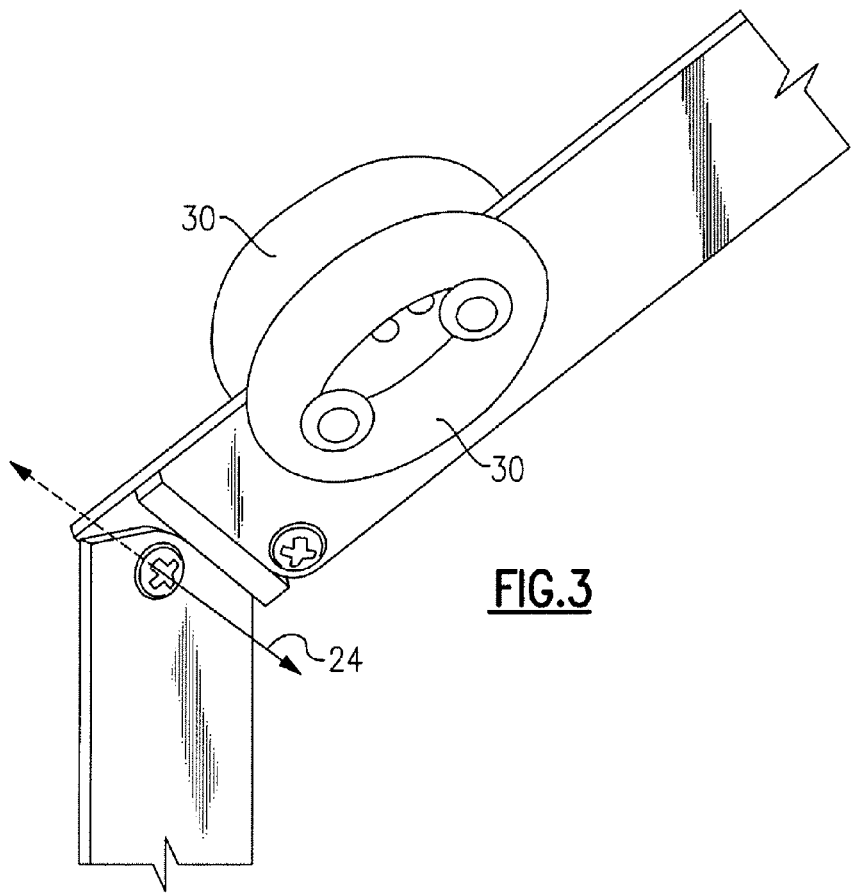
FIG. 3 is a perspective view of the knee brace in a rotated position.

As will be appreciated, the present invention provides an effective device for assisting a skier in re-positioning his legs as he skis. Reference is made to FIGS. 1 and 2, which illustrate a hinge assembly 10 of a knee brace 11 (shown in FIG. 5) in a cut-away view to more clearly show operation of knee brace 11. Hinge assembly 10 comprises three main sections or segments, which affect movement of the wearer's leg. Upper segment 12 is connected to a middle linking or hinging segment 14 by a pivot pin 16, permitting rotation about a horizontal axis 18. A lower segment 20 is connected to middle segment 14 by a pivot pin 22, permitting rotation around a horizontal axis 24. Each pivot pin, 16 and 22, may include a shank for passing through the pivot openings and a cap or head section securely fitted to each end of the shank for maintaining the shank in the opening. The shank is loosely fitted in the opening to allow relative pivotal movement of the hinge members. A stop 26 may be located on middle segment 16 to provide support for upper segment 14.

Anchor pin 28 is positioned in upper segment 12 and anchor pin 29 is positioned in middle segment 14 for anchoring a bias member, which may be a spring, elastic band or the like. Elastic bands 30 are shown positioned on anchor pins 28 and 29 in the Figures. When upper segment 12 and middle segment 14 are in parallel alignment with the longitudinal axis 32 of middle segment 14, the segments are in a neutral or predetermined position. In this neutral position, the elastic bands 30 are in a normal, unbiased state. As clearly shown in FIG. 2, upper segment 12 shows a notch 34 for allowing the positioning of anchor pin 29 on middle segment 14. As a result, the lower ends of elastic bands 30 are positioned on middle segment 14 and the upper ends of elastic bands 30 are positioned on upper segment 12. This creates biasing of upper segment 12 and middle segment 14 by bands 30 when segment 12 rotates about axis 18.

Figure 4:
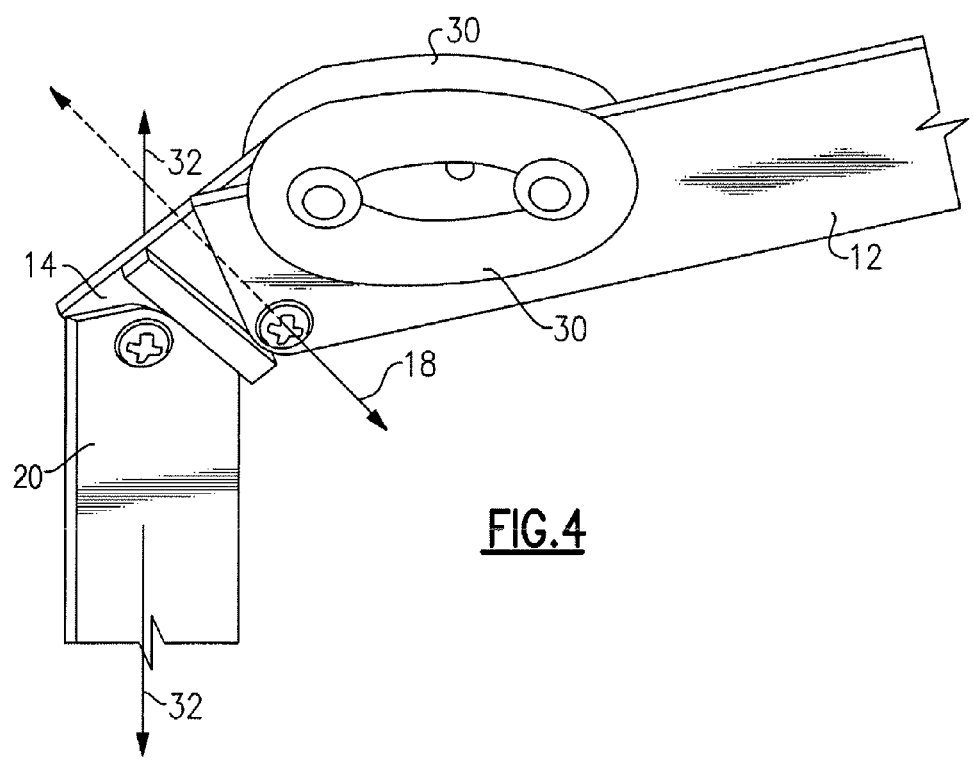
FIG. 4 is a perspective view of the knee brace of FIG. 3 in a succeeding rotated position.

FIGS. 3 and 4 illustrate the rotation of hinge assembly 10. FIG. 3 shows rotation of upper segment 12 and middle segment 14 about axis 24. Elastic bands 30 are maintained in neutral or unbiased position as segments 12 and 14 rotate about axis 24. FIG. 4 illustrates rotation of upper segment 12 about axis 18. As segment 12 rotates about axis 18, it is no longer aligned along the longitudinal axis 32 of middle segment 14. This causes elastic bands 30 to extend, creating a state of tension. The resiliency of elastic bands 30 will bias segment 12 to its neutral upright position and re-align it with segment 14.

Reference is made to FIGS. 1 and 2, which show openings 40 and 41 for placement of anchor pin 28 in order to provide options for the placement of anchor pins therein. This allows one to vary or adjust the tension provided by the biasing member. As shown in the Figures, anchor pin 28 is located furthest from the proximal end 42 of upper segment 12 in order to create the highest amount of tension, when upper segment 12 is rotated about axis 18. If less tension is desired upon rotation of segment 12, anchor pin 28 may be inserted into opening 40 or 41 to provide less distance between pin 29 and pin 28. As the rotation increases, the tension increases, and a greater force will react to "pull back" segment 12 to its upright position.

Figure 5:
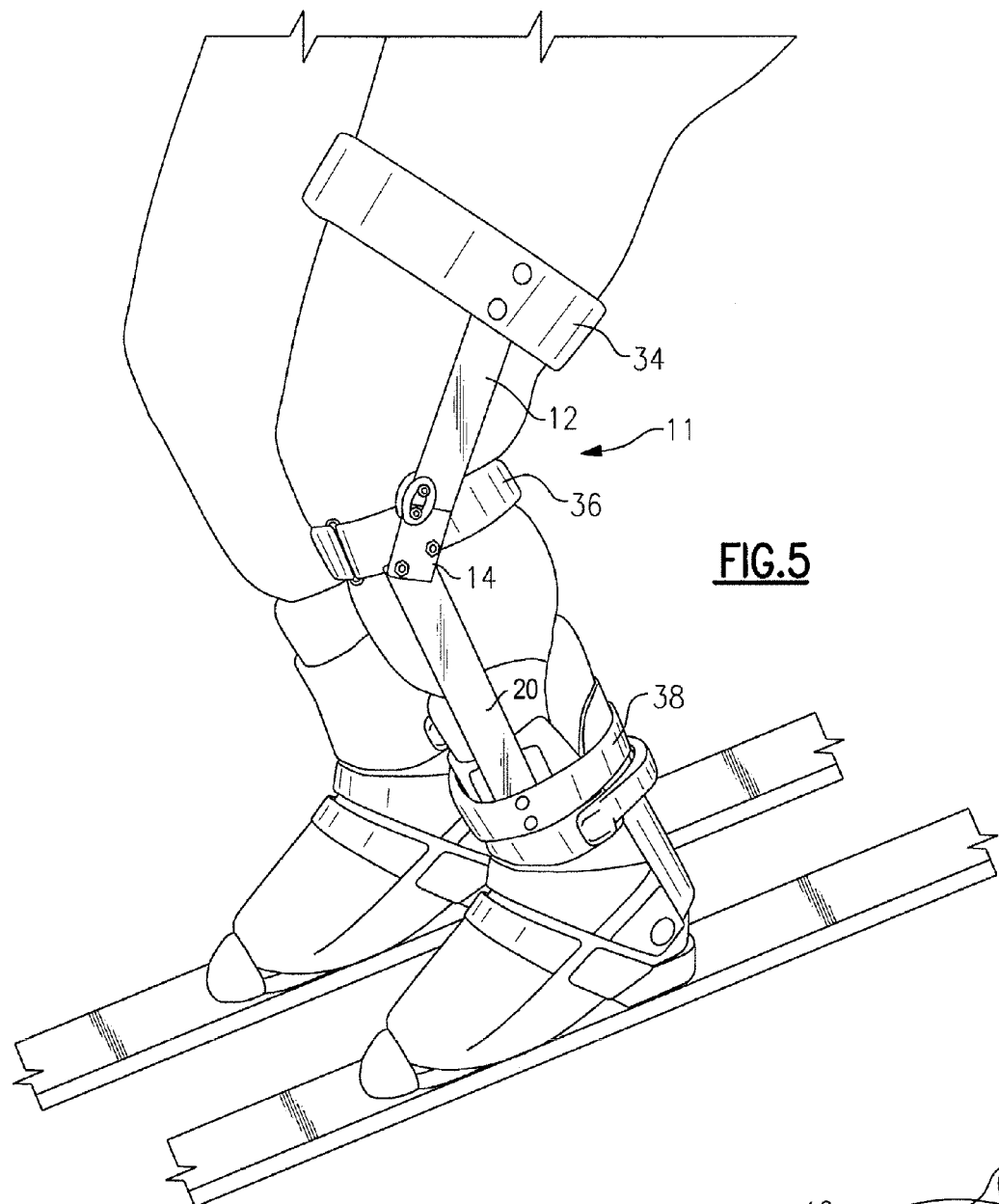
FIG. 5 is a perspective view of the knee brace in use on a wearer's leg.

FIG. 5 shows knee brace 11 in position on a wearer's leg. Hinge assembly 10 is positioned on the lateral side of the knee (as shown), and also on the medial side of the knee to provide support along both sides of the leg. The placement of the hinge assembly 10 is preferably proximate the wearer's knee joint, such that the hinge assembly 10 is flexed at generally the same location at which the knee is bent. The lower end of band 30 is positioned at or just slightly above pivot axis 18 of segment 14 and also proximate the knee joint. Due to resiliency of hinge assembly 10, the leg is urged in generally straight configuration when the leg is bent.

Figure 6:
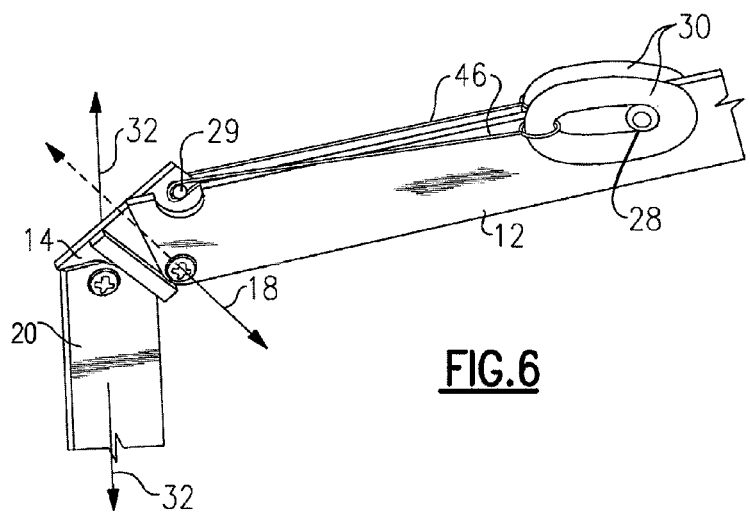
FIG. 6 is a perspective view of the knee brace with an alternate biasing mechanism.

In an alternate embodiment of the present invention, reference is made to FIG. 6, which shows band 30 attached to a string or cable 46. Cable 46 is positioned on anchor pin 29 at one end and is connected to elastic band 30 at the other end. Elastic band 30 is also positioned on anchor pin 28, which pin 28 is located a further distance from anchor pin 29 and from the axis of rotation of axis 18. The connection of elastic band 30 to cable 46 allows for more flexibility and less tension in the rotation of axis 18. This is optimal for a user who would like less tension applied when bending his knees, but would still desire a slight force to assist in the straightening of his knees. This provides more options and variations for users, who vary in weight, strength and flexibility in their legs, and/or desire less force to straighten their legs.

In order to attach the brace to a wearer's knee, a series of collars or straps may be used. As shown in FIG. 5, straps 34, 36 and 38 are positioned at the thigh, knee and ankle, respectively, of the wearer. Although three separate straps are shown in FIG. 5, it is possible that fewer or greater than three may be used to attach knee brace 10 to the wearer's leg. Also, the location of the strap onto the wearer's leg may vary somewhat from the thigh, knee and ankle areas, such as near the calf area, as long as the attachment is effective and comfortable. For example, strap 38 positioned proximate the wearer's ankle could be located closer to strap 36, more proximate the wearer's knee. The straps can be adjusted to provide a snug fit about the wearer's thigh, knee or calf and/or ankle area.

The straps and hinge segments may be made of a lightweight thermoplastic material, lightweight metal, plastic, composite or other similar material. The strap and hinge members may be formed of substantially rigid, or alternatively may be flexible. The straps and hinge segments may be made of the same or different materials. Some examples include lightweight aluminum metal, nylon, polypropylene, polyethylene, and composites thereof, including fiber reinforced composites with glass, carbon, and/or polymeric fibers therein. As a means of attachment, the straps may include an elastic or an inelastic material with a hook and loop fastener, such as a Velcro® fastener to secure the ends of the attachment straps, for easy adjustment for any size leg. Padding may be added to the straps and/or the hinge assembly to prevent direct contact between the hinge assembly and the wearer's leg. The straps may be attached to the hinge assembly by adhesive, rivets, snaps or similar fastening mechanism.

Once the knee brace is fitted to the wearer's leg, the wearer will have full range of flexion and extension. The movement of knee brace 11 is dependent on the movement of the wearer's knee. In FIG. 5, the wearer's knee is slightly bent, showing rotation of segments 12 and 14 about axis 24 (as more clearly shown in FIG. 3). As the wearer further flexes his knee, segment 12 will rotate about axis 18 as shown in FIG. 4, creating tension in bands 30. A counteractive force will bias or pull segment 12 to a more upright position, in parallel alignment with the longitudinal axis of segment 14. The wearer will feel slight pressure from the brace, which will enable the wearer to straighten his leg. The force created to re-align segment 12 in a more upward or in ascending position will assist the wearer in extending or straightening his leg.

The knee brace is very useful for a downhill skier. As skier typically serpentines a mountain, he will repeatedly bend and extend his knees. As the skier bends his knees, the resiliency of the bands will pull the skier's legs back to a straight position. This will assist the skier in "pulling out" of his turns. This brace is useful for someone learning to ski, or for people who may have weak or tired legs.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A knee brace comprising:
a hinge assembly comprising (i) an upper segment having a top and a bottom and an exterior side; (ii) a lower segment having a top and a bottom; (iii) a middle linking segment having a top and a bottom and an interior side and extending along a longitudinal axis and coupled to the upper and lower segments to permit pivotal movement of the upper segment relative to the lower segment; and (iv) one or more biasing members each having an upper end and a lower end and each being anchored to the upper and middle linking segments to resiliently bias the upper and middle segments toward a predetermined alignment; (v) a first anchor pin disposed through the middle linking segment; and (vi) a second anchor pin disposed through the upper segment for positioning the biasing members thereon, wherein the first and second pins are disposed in linear vertical alignment when the middle and upper segments are in axial alignment along the longitudinal axis of the middle linking segment and a series of straps to strap the upper, lower and middle segments to a wearer's leg.

2. The knee brace of claim 1 wherein the one or more biasing members comprise a first and second biasing member disposed opposite to one another, whereby the first biasing member is disposed proximate the exterior side of the upper segment on the first and second anchor pins and whereby the upper end of the second biasing member is disposed proximate the interior side of the upper segment and the lower end of the second biasing member is disposed proximate the exterior side of the middle segment on first and second anchor pins.

3. The knee brace of claim 1 whereby a first pivot pin connects the lower segment to the middle linking segment and a second pivot pin connects the middle linking segment to the upper segment.

4. The knee brace of claim 3 whereby the upper and middle segments rotate about a first horizontal axis created by the first pivot pin.

5. The knee brace of claim 4 whereby the upper segment further rotates about a second horizontal axis created by the second pivot pin.

6. The knee brace of claim 5 whereby the rotation of the upper segment away from the predetermined alignment causes tension in the one or more biasing members, whereby the upper and middle segments are biased back toward the predetermined alignment.

7. The knee brace of claim 5 whereby the lower end of the biasing member is positioned at or slightly above the second horizontal axis created by the second pivot pin.

8. The knee brace of claim 1 whereby the series of straps comprise a first strap connected to the upper segment proximate the top thereof for placement at the wearer's thigh; a second strap connected to the middle linking segment proximate the bottom thereof and connected to the lower segment proximate the bottom thereof for placement below the wearer's knee; and a third strap connected to the lower segment proximate the bottom thereof for placement at the wearer's ankle.

9. The knee brace of claim 1 wherein the upper segment comprises a plurality of first openings in linear vertical alignment for placement of anchor pins therein.

10. The knee brace of claim 9 wherein the middle linking segment comprises a second opening in linear vertical alignment with the plurality of first openings in the upper segment when the middle and upper segments are in axial alignment along the longitudinal axis of the middle linking segment.

11. The knee brace of claim 1 whereby the predetermined alignment of the upper and middle segments comprises the middle and upper segments in vertical and axial alignment along the longitudinal axis of the middle segment.

12. The knee brace of claim 1 wherein the one or more biasing members comprise elastic bands or springs.

13. The knee brace of claim 12 wherein the bands or springs comprise a first end and a second end, whereby the first end of the bands or springs are connected to cables or strings, whereby the cables or strings anchor the bands or springs to the middle segment and whereby the second end of the bands or springs anchor the bands or springs to the upper segment.

14. The knee brace of claim 1 whereby the hinge assembly is located on both the lateral and medial sides of the knee brace.

15. The knee brace of claim 1 wherein the upper, lower and middle segments are fabricated of lightweight aluminum metal, nylon, polypropylene, polyethylene, or a composite thereof.

16. The knee brace of claim 15 wherein the composite comprises fibers selected from the group consisting of glass, carbon, polymeric fibers and mixture thereof.

17. The knee brace of claim 1 wherein the series of straps are fabricated of lightweight aluminum metal, nylon, polypropylene, polyethylene, or a composite thereof.

18. The knee brace of claim 17 wherein the composite comprises fibers selected from the group consisting of glass, carbon, polymeric fibers and mixture thereof.

19. The knee brace of claim 17 whereby the series of straps include a fastener to faster the knee brace to the wearer's leg.

20. The knee brace of claim 19 wherein the fastener comprises a hook and loop fastener.

21. The knee brace of claim 1 whereby the hinge assembly is fastened to the straps by adhesive, rivets or snaps.

22. A knee brace comprising:
a hinge assembly comprising (i) an upper segment having a top and a bottom and an exterior side; (ii) a lower segment having a top and a bottom; (iii) a middle linking segment having a top and a bottom and an interior side and extending along a longitudinal axis and coupled to the upper and lower segments to permit pivotal movement of the upper segment relative to the lower segment; and (iv) one or more biasing members each having an upper end and a lower end and each being anchored to the upper and middle linking segments to resiliently bias the upper and middle segments toward a predetermined alignment, wherein the upper segment comprises a plurality of first openings in linear vertical alignment for placement of anchor pins therein; and
a series of straps to strap the upper, lower and middle segments to a wearer's leg.

23. A knee brace comprising:
a hinge assembly comprising (i) an upper segment having a top and a bottom and an exterior side; (ii) a lower segment having a top and a bottom; (iii) a middle linking segment having a top and a bottom and an interior side and extending along a longitudinal axis and coupled to the upper and lower segments to permit pivotal movement of the upper segment relative to the lower segment; and (iv) one or more biasing members each having an upper end and a lower end and each being anchored to the upper and middle linking segments to resiliently bias the upper and middle segments toward a predetermined alignment; and
a series of straps to strap the upper, lower and middle segments to a wearer's leg;
whereby a first pivot pin connects the lower segment to the middle linking segment and a second pivot pin connects the middle linking segment to the upper segment;
whereby the upper and middle segments rotate about a first horizontal axis created by the first pivot pin;
whereby the upper segment further rotates about a second horizontal axis created by the second pivot pin; and
whereby the lower end of the biasing member is positioned at or slightly above the second horizontal axis created by the second pivot pin.

24. A knee brace comprising:
a hinge assembly comprising (i) an upper segment having a top and a bottom and an exterior side; (ii) a lower segment having a top and a bottom; (iii) a middle linking segment having a top and a bottom and an interior side and extending along a longitudinal axis and coupled to the upper and lower segments to permit pivotal movement of the upper segment relative to the lower segment; and (iv) one or more biasing members each having an upper end and a lower end and each being anchored to the upper and middle linking segments to resiliently bias the upper and middle segments toward a predetermined alignment; and
a series of straps to strap the upper, lower and middle segments to a wearer's leg;

wherein the one or more biasing members comprise elastic bands or springs; and wherein the bands or springs comprise a first end and a second end, whereby the first end of the bands or springs are connected to cables or strings, whereby the cables or strings anchor the bands or springs to the middle segment and whereby the second end of the bands or springs anchor the bands or springs to the upper segment.

* * * * *